United States Patent
Sato

(10) Patent No.: US 7,873,408 B2
(45) Date of Patent: Jan. 18, 2011

(54) BIOIMAGING APPARATUS

(75) Inventor: Hideo Sato, Tokyo (JP)

(73) Assignee: Sony Corporation, Tokyo (JP)

( * ) Notice: Subject to any disclaimer, the term of this patent is extended or adjusted under 35 U.S.C. 154(b) by 557 days.

(21) Appl. No.: 11/722,119

(22) PCT Filed: Dec. 8, 2005

(86) PCT No.: PCT/JP2005/022996

§ 371 (c)(1), (2), (4) Date: Jun. 19, 2007

(87) PCT Pub. No.: WO2006/070605

PCT Pub. Date: Jul. 6, 2006

(65) Prior Publication Data

US 2009/0093727 A1    Apr. 9, 2009

(30) Foreign Application Priority Data

Dec. 28, 2004    (JP) .............................. 2004-381430

(51) Int. Cl.
*A61B 6/00*    (2006.01)
*G06T 1/00*    (2006.01)
*G06T 7/00*    (2006.01)

(52) U.S. Cl. ..................... 600/476; 340/5.83

(58) Field of Classification Search .............. 340/5.52, 340/5.82, 5.83; 600/476; 902/3; 382/115–124; 356/71, 448, 300, 432, 433
See application file for complete search history.

(56) References Cited

U.S. PATENT DOCUMENTS

| | | | | |
|---|---|---|---|---|
| 4,728,186 A | * | 3/1988 | Eguchi et al. | 356/71 |
| 4,924,085 A | * | 5/1990 | Kato et al. | 250/227.28 |
| 4,972,569 A | | 11/1990 | Aoki et al. | |
| 5,177,802 A | * | 1/1993 | Fujimoto et al. | 382/124 |
| 6,041,247 A | * | 3/2000 | Weckstrom et al. | 600/323 |
| 7,245,745 B2 | * | 7/2007 | Nagasaka et al. | 382/115 |
| 2001/0037811 A1 | * | 11/2001 | Beuthan et al. | 128/897 |

(Continued)

FOREIGN PATENT DOCUMENTS

CN    1527247    9/2004

(Continued)

OTHER PUBLICATIONS

European Search Report corresponding to European Serial No. 05814366 dated Sep. 14, 2009.

(Continued)

*Primary Examiner*—Long V Le
*Assistant Examiner*—Jacqueline Cheng
(74) *Attorney, Agent, or Firm*—SNR Denton US LLP

(57) ABSTRACT

To improve image quality as well as considering miniaturization. In the top surface 2A of a housing 2, a placing part 7 is provided near other end of shorter side ED2. A reflective board 6 is provided between an imaging opening part 3 facing to the above placing part 7 and one end of shorter side ED1. And in the housing 2 at a lower part of the above imaging opening part 3, a CCD image pickup device 4 for transmitting near infrared lights that passed through a finger FG placed on the placing part and was refracted by the reflective board 6 as a blood vessel image signal S1 is provided.

12 Claims, 8 Drawing Sheets

U.S. PATENT DOCUMENTS

| | | | |
|---|---|---|---|
| 2003/0016345 A1 | 1/2003 | Nagasaka et al. | |
| 2004/0057605 A1 | 3/2004 | Kono et al. | |
| 2004/0184641 A1 | 9/2004 | Nagasaka et al. | |
| 2004/0220479 A1 | 11/2004 | Wake et al. | |
| 2005/0180620 A1* | 8/2005 | Takiguchi | 382/128 |

FOREIGN PATENT DOCUMENTS

| | | |
|---|---|---|
| DE | 38 80 483 | 11/1988 |
| DE | 103 32 106 | 9/2004 |
| EP | 0150697 | 8/1985 |
| EP | 0 347 469 | 12/1989 |
| EP | 0833274 | 4/1998 |
| JP | 1-503203 | 1/1989 |
| JP | 3100993 | 8/2000 |
| JP | 2001-142606 | 5/2001 |
| JP | 2004-110605 | 4/2004 |
| JP | 2004-265269 | 9/2004 |
| JP | 2005-253988 | 9/2005 |
| JP | 2005-253989 | 9/2005 |
| JP | 2006-011711 | 1/2006 |
| WO | 88/04153 | 6/1988 |
| WO | 89/05198 | 11/1988 |
| WO | WO03096272 | 11/2003 |

OTHER PUBLICATIONS

International Search Report dated Jan. 17, 2006.
Japanese Office Action issued on Jun. 3, 2010 in connection with counterpart JP Appl. No. 2004-381430.

\* cited by examiner

BIOIMAGING APPARATUS

TECHNICAL FIELD

The present invention relates to a bioimaging apparatus, and is suitably applied to biometrics authentication, for example.

BACKGROUND ART

In recent years, blood vessels existing inward of a living body is aimed for one of the objects of biometrics authentication.

Deoxygenetated hemoglobin (venous blood) or oxygeneted hemoglobin (arterial blood) flowing in a blood vessel has a property that uniquely absorbs lights in a near infrared band (near infrared lights). An imaging apparatus for picking up the image of blood vessels by using this property has been proposed.

Concretely, an imaging apparatus in which near infrared lights are emitted to a finger being placed on an imaging opening from a light source of near infrared light, the lights are reflected or dispersed inward of this finger, and near infrared lights entered in a housing passed through the above finger and the imaging opening are induced on the imaging plane of an image pickup device via an optical lens, so that blood vessels are imaged has been proposed (see Japanese Patent Laid-Open No. 2004-195792 (see FIGS. 2 and 15, for example.)

By the way, in an imaging apparatus having the above configuration, distortion of aberration in an optical system caused by that the distance between the finger and the image pickup device is short is corrected by a macro lens and signal processing. However, there is a limit in the reproducibility. Thus, there is a problem that improvement in image quality above a certain degree cannot be expected. More particularly, if considering that the images of blood vessels will be used as objects to be authenticated or a part of data in medical diagnosis, the problem of image quality is further serious.

On the other hand, if it is tried to physically keep the distance between the imaging opening and the object to be imaged, the thickness of the overall imaging apparatus increases for that. It is not agree with a demand for miniaturization in recent years. More particularly, it is not adequate in the case of installing the above imaging apparatus in a portable terminal device such as a cellular phone in that a demand for reduction in thickness is strong.

DISCLOSURE OF INVENTION

Considering the above point, the present invention has been done, and provides a bioimaging apparatus in that image quality can be improved while considering miniaturization.

To solve the above problem, according to the present invention, in a bioimaging apparatus for imaging a formation in a bioregion as an object to be imaged, a placing part that is provided on the front surface side of a housing containing an electronic circuit to place the bioregion, an emitting part for emitting imaging lights to the placing part, a reflective board that is provided on the front surface side of the housing as facing to the placing part and reflects the imaging lights from the bioregion placed on the placing part to the inner side of the housing, and an image pickup device that is provided in the housing and transmits the imaging lights reflected by the reflective board as an image signal are provided.

Accordingly, in this bioimaging apparatus, in addition to the distance from the image pickup device to the reflective board in the thickness direction, the distance from the reflective board to the placing part in the horizontal direction can be kept. Therefore, distortion of aberration in the optical system can be removed without only relying on correction by a macro lens and a signal processing circuit, as well as restraining the overall thickness.

Further, according to the present invention, in a bioimaging apparatus for imaging a formation in a bioregion as an object to be imaged, a placing part that is provided on the front surface side of a housing containing an electronic circuit to place the bioregion, an emitting part for emitting imaging lights to the placing part, and an image pickup device that is provided on the front surface side of the housing as facing to the placing part and transmits the imaging lights from the bioregion placed on the placing part as an image signal are provided.

Accordingly, in this bioimaging apparatus, a distance can be kept on the front surface side of the above housing in the horizontal direction, without containing an imaging system such as an emitting part and an image pickup device in a housing containing an electronic circuit. Therefore, distortion of aberration in the optical system can be removed without only relying on correction by a macro lens and a signal processing circuit, as well as reducing the thickness of the above housing itself and restraining the overall thickness.

According to the present invention, in a bioimaging apparatus for imaging a formation in a bioregion as an object to be imaged, a placing part that is provided on the front surface side of a housing containing an electronic circuit to place the bioregion, an emitting part for emitting imaging lights to the placing part, a reflective board that is provided on the front surface side of the housing as facing to the placing part and reflects the imaging lights from the bioregion placed on the placing part to the inside of the housing, and an image pickup device that is provided in the housing and transmits the imaging lights reflected by the reflective board as an image signal are provided. Thereby, in addition to the distance from the CCD image pickup device to the reflective board in the thickness direction, the distance from the reflective board to the placing part can be kept in the horizontal direction. Therefore, distortion of aberration in an optical system can be removed without only relying on correction by a macro lens and a signal processing circuit, as well as restraining the overall thickness. Thus, image quality can be improved while considering miniaturization.

Further, according to the present invention, in a bioimaging apparatus for imaging a formation in a bioregion as an object to be imaged, a placing part that is provided on the front surface side of a housing containing an electronic circuit to place the bioregion, an emitting part for emitting imaging lights to the placing part, and an image pickup device that is provided on the front surface side of the housing as facing to the placing part and transmits the imaging lights from the bioregion placed on the placing part as an image signal are provided. Thereby, a distance can be kept on the front surface side of the above housing in the horizontal direction, without containing an imaging system such as an emitting part and an image pickup device in a housing containing an electronic circuit. Therefore, distortion of aberration in the optical system can be removed without only relying on correction by a macro lens and a signal processing circuit, as well as reducing

BEST MODE FOR CARRYING OUT THE INVENTION

An embodiment to which the present invention is applied will be described in detail, with reference to the accompanying drawings.

(1) First Embodiment

(1-1) Exterior Configuration of Authentication Apparatus

Figure 1:
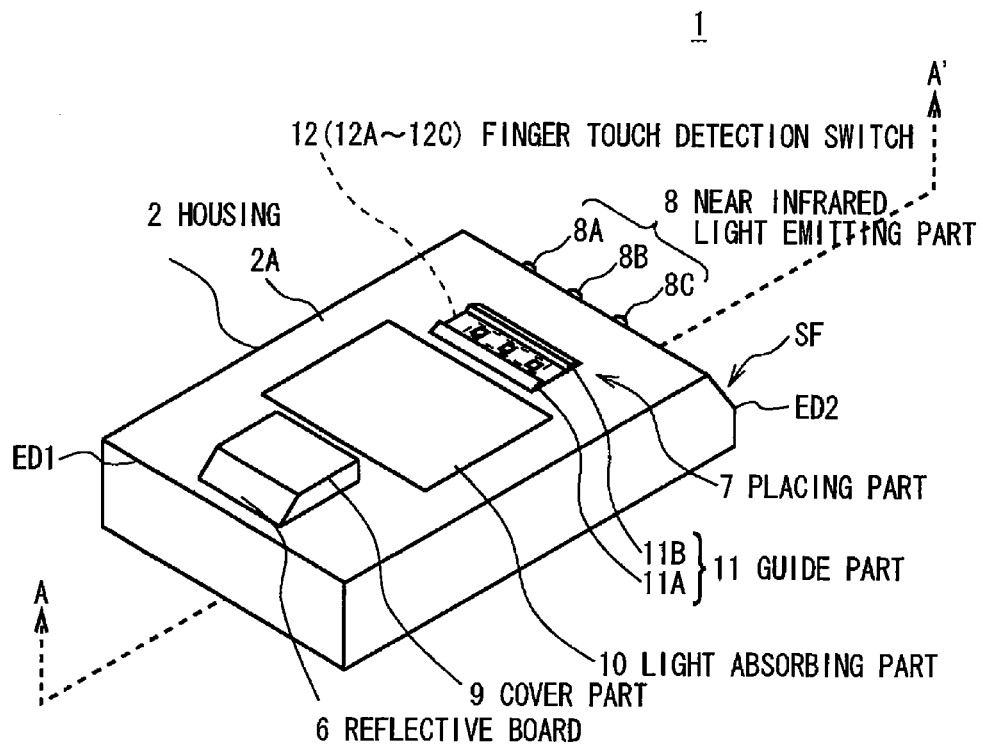
FIG. 1 is a schematic diagram showing the exterior configuration (1) of an authentication apparatus.
Figure 2:
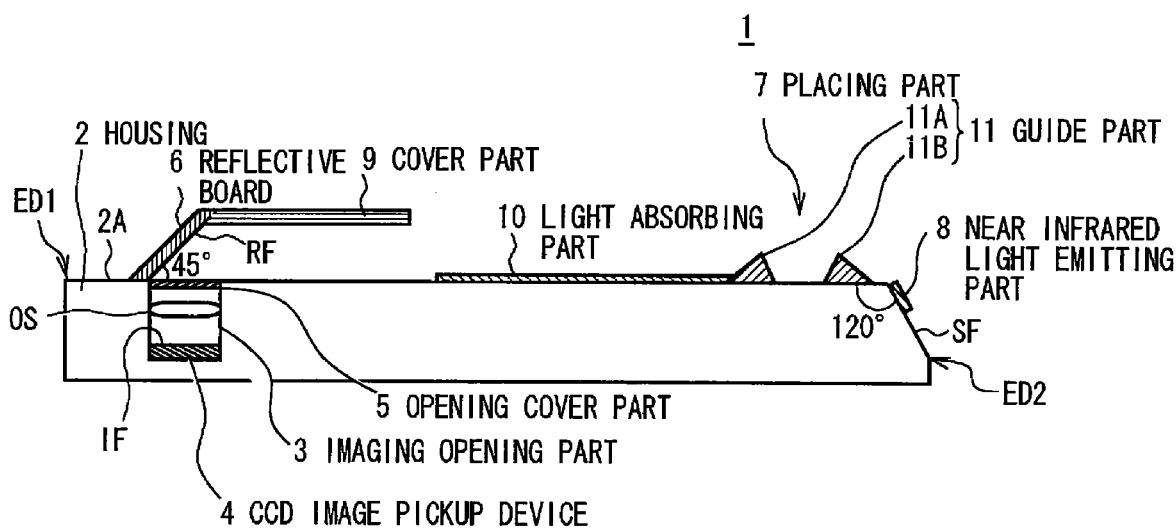
FIG. 2 is a schematic diagram showing the exterior configuration (2) of the authentication apparatus.

Referring to FIG. 1 and FIG. 2 that is a section by A-A' in this FIG. 1, the reference numeral 1 shows an authentication apparatus according to a first embodiment as a whole. In a housing 2 in an almost rectangular parallelepiped shape, at a position near one end of shorter side ED1, an imaging opening part 3 is formed as extending from a top surface 2A to the inside of the housing 2. On the bottom surface of this imaging opening part 3, a CCD (Charge Coupled Device) image pickup device 4 is disposed.

Between this imaging opening part 3 and the CCD image pickup device 4, an optical system part OS composed of a lens, a diaphragm and an object lens that have a macro lens function and a filter function to selectively transmit near infrared lights are provided. On the surface of the imaging opening part 3, a white and transparent opening cover part 5 made of predetermined material is provided. Thereby, that a foreign object comes in the housing 2 from the imaging opening part 3 can be prevented, and the optical system part OS and the CCD image pickup device 4 can be protected.

On the other hand, between the imaging opening part 3 and the one end of shorter side ED1, a board-form reflective board 6 is provided as inclined to other end of shorter side ED2 so as to have an inclination angle of 45 degrees to the top surface 2A. At a position near the above other end of shorter side ED2, a placing part 7 to place a finger is provided. Between the above placing part 7 and the other end of shorter side ED2, three near infrared light emitting parts 8 (8A, 8B and 8C) for emitting near infrared lights uniquely absorbed by hemoglobin to the placing part 7 as imaging lights of blood vessels are provided.

Figure 3:
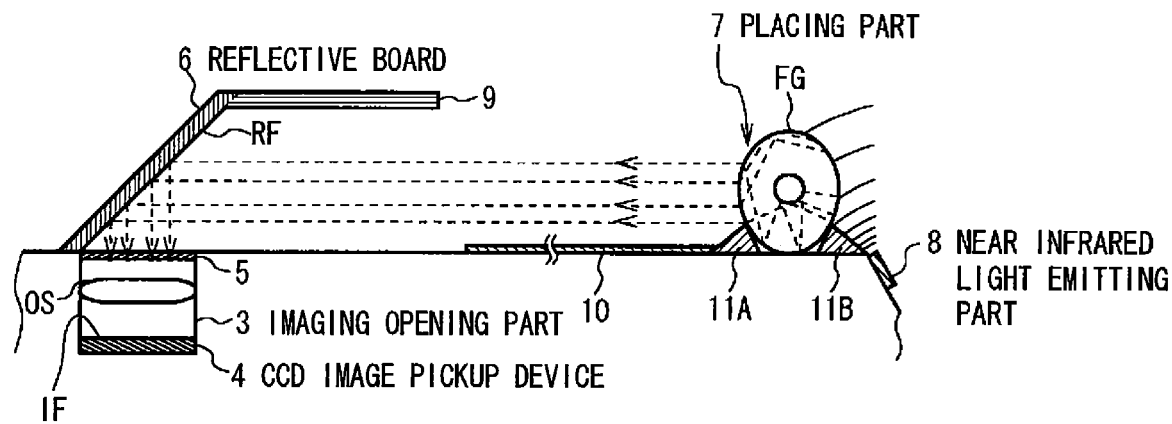
FIG. 3 is a schematic diagram for explaining the light path of near infrared lights.

Thereby, in this authentication apparatus 1, as shown in FIG. 3, if a finger FG is placed on the placing part 7, near infrared lights emitted from the near infrared light emitting parts 8 are irradiated to the above finger FG. The lights are absorbed by hemoglobin flowing in blood vessels existing inward of the finger FG, and pass through the inside of the finger FG by reflected and dispersed in tissues other than the blood vessels, and are emitted out of the above finger FG as near infrared lights projecting the blood vessels (hereinafter, this is referred to as "blood vessel projecting lights"). Then, the blood vessel projecting lights that are almost parallel to the top surface 2A are refracted by a reflecting surface RF of the reflective board 6, and are incident on the imaging surface IF of the CCD image pickup device 4 sequentially via the opening cover part 5 and the optical system part OS. As a result, in this authentication apparatus 1, the image of the blood vessels inward of the finger FG placed on the placing part 7 is formed on the imaging surface IF of the CCD image pickup device 4.

The CCD image pickup device 4 picks up the image of the blood vessels formed on the imaging surface IF, and transmits thus obtained signal to an electronic circuit contained in the housing 2 as a blood vessel image signal.

In this manner, the authentication apparatus 1 can image the blood vessels inward of the finger FG.

(1-2) Countermeasure to Improve Image Quality

In addition to the above configuration, in this authentication apparatus 1, various countermeasures to improve image quality are taken in order to obtain fine imaging results.

Practically, as also obvious from FIGS. 1 and 2, in the reflective board 6, a cover part 9 which covers the reflecting surface RF except for the incident path and the reflecting path of imaging lights (near infrared lights) to the reflecting surface RF is formed in one body. Thereby, in this authentication apparatus 1, the situation that lights in the atmosphere enter to the imaging opening part 3 can be prevented. Therefore, blood vessels in a living body can be imaged without including noise components caused by the above lights in the atmosphere in a blood vessel image signal.

Then, between the reflective board 6 and the placing part 7, a sheet-form light absorbing part 10 is laid. Thus, in this authentication apparatus 1, the situation that lights in the atmosphere go to the reflective board 6 as reflecting lights from the top surface 2A can be prevented. At the same time, in blood vessel projecting lights emitted by passing through the inside of the finger FG, blood vessel projecting lights that are almost parallel to the top surface 2A can be further selectively emitted to the imaging surface IF of the CCD image pickup device 4. Thereby, the blood vessels in the living body can be further faithfully imaged.

Note that, in this authentication apparatus 1, the top surface 2A is not isolated from the outside as a whole. Therefore, the situation that in the case of isolated, in its inside, near infrared lights which were reflected without passing through the finger FG are emitted to the imaging surface IF of the CCD image pickup device 4 via the reflective board 6 can be avoided.

Further, on the top surface 2A providing the near infrared light emitting parts 8, a slant surface SF having an inclination angle of 120 degrees to the above top surface 2A is formed. Thereby, in this authentication apparatus 1, as also obvious from FIG. 3, near infrared lights are emitted to the surface of the finger FG placed on the placing part 7 from an oblique direction. Therefore, in this authentication apparatus 1, in comparison to the case of emitting them from the direction parallel to the top surface 2A, reflecting lights to the surface of the finger FG can be vastly reduced, and also further more blood vessel projecting lights can be emitted from the above finger FG. Thus, the blood vessels in the living body can be further faithfully imaged.

Then, these near infrared light emitting parts 8 emit near infrared lights in an wavelength band that will be uniquely absorbed by both of oxygenated hemoglobin and deoxygenated hemoglobin (approximately 900 [nm]-1000 [nm]). Thereby, in this authentication apparatus 1, both of blood vessels in a venous system and an arterial system that are mixed in the ends of a living body can be faithfully imaged.

Figure 4:
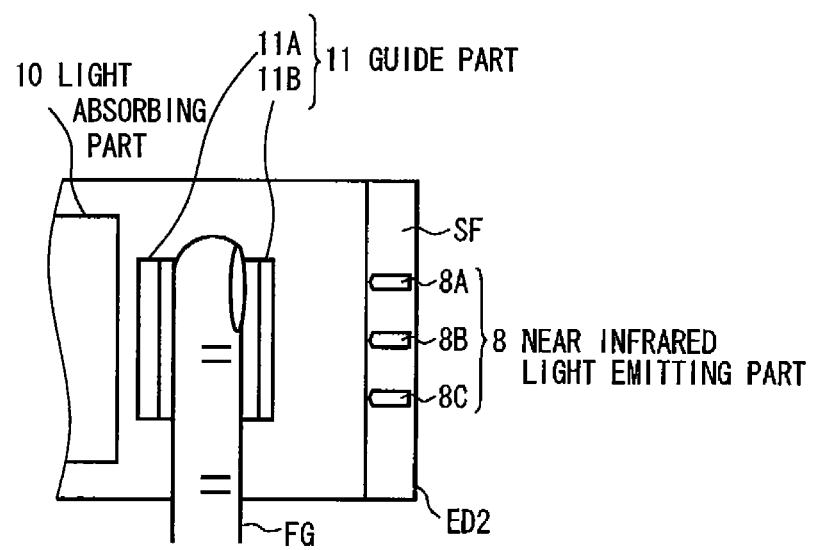
FIG. 4 is a schematic diagram for explaining a placement of a finger.

Further, in the placing part 7, a pair of guide parts 11 (11A and 11B) to guide a finger FG so that the belly of the finger FG is orthogonal to the top surface 2A are formed. Thereby, in this authentication apparatus 1, as shown in FIG. 4, the side of the finger FG can be placed on the placing part 7. Thus, bloodstream stop caused by that a user strongly pressed the finger FG on the placing part 7 can be prevented, in comparison to the case of placing the belly of the above finger FG. Consequently, blood vessels in a living body can be certainly imaged.

Further, between this pair of guide parts 11, as also obvious from FIG. 1, three switches for detecting a touch of a finger FG (hereinafter, this is referred to as "finger touch detection switches") 12 (12A, 12B and 12C) are provided along the guide direction at predetermined intervals. In this authentication apparatus 1, in the case where being a finger FG parallel was recognized based on detection results by these finger touch detection switches 12A, 12B and 12C, imaging of the above finger FG can be started.

Thereby, in this authentication apparatus 1, a finger can be imaged in the same inclination of the finger without depending on the person to be imaged. Consequently, correcting processing on an imaging result (blood vessel image signal S1) such as turning the image after the above imaging can be omitted.

(1-3) Circuit Configuration of Authentication Apparatus

Figure 5:
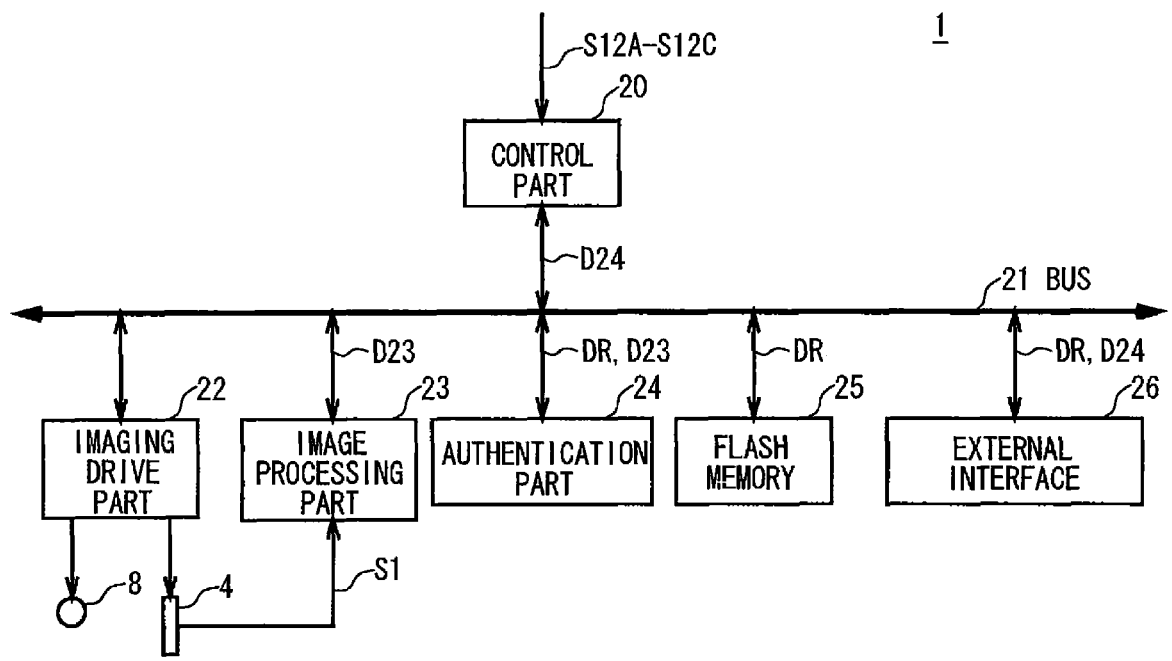
FIG. 5 is a block diagram showing the circuit configuration of the authentication apparatus.

Next, FIG. 5 shows the circuit configuration of the authentication apparatus 1.

Referring to FIG. 5, the authentication apparatus 1 is formed by that an imaging drive part 22, an image processing part 23, an authentication part 24, a flash memory 25 and an interface for transmitting/receiving data to/from external devices (hereinafter, this is referred to as an "external interface") 26 are connected to a control part 20 via a bus 21 respectively.

This control part 20 has a computer configuration including a CPU (Central Processing Unit) for controlling the entire authentication apparatus 1, a ROM (Read Only Memory) in that various programs are stored, and a RAM (Random Access Memory) serving as a work memory of the above CPU. Corresponding detection signals S12A, S12B and S12C are supplied to the above control part 20, from the three finger touch detection switches 12A, 12B and 12C (FIG. 1) respectively.

Further, from an external management system (not shown) for managing registered blood vessel images in a database via the external interface 26, data of the above registered blood vessel image (hereinafter, this is referred to as "registered blood vessel image data") DR is supplied to the control part 20.

Then, if the above registered blood vessel image data DR is supplied, the control part 20 shifts an operation mode to a blood vessel registration mode and controls the flash memory 25 based on a corresponding program stored in the ROM, and stores the above registered blood vessel image data DR in the flash memory 25 for holding.

On the other hand, in the case where all of the corresponding detection signals S12A, S12B and S12C were supplied from the three finger touch detection switches 12A, 12B and 12C (FIG. 1), the control part 20 recognizes that the finger FG is parallel. The control part 20 shifts the operation mode to an authentication mode, and controls the imaging drive part 22, the image processing part 23 and the authentication part 24 respectively, based on a corresponding program stored in the ROM. At the same time, the control part 20 reads the registered blood vessel image data DR registered in the flash memory 25 and transmits this to the authentication part 24.

In this case, the imaging drive part 22 drives the near infrared light emitting parts 8 and the CCD image pickup device 4 respectively. As a result, from the near infrared light emitting parts 8, near infrared lights are emitted to the finger FG placed between the pair of guide parts 11A and 11B (FIG. 3) at this time, and blood vessel projecting lights induced to the imaging surface IF of the CCD image pickup device 4 (FIG. 3) via the above finger FG is transmitted from the CCD image pickup device 4 to the image processing part 23, as a blood vessel image signal S1.

The image processing part 23 sequentially performs for example, analog-to-digital conversion processing, various filtering processing for noise component elimination and outline emphasis, binarization processing, and blood vessel linearization processing called Morphology, on the blood vessel image signal S1. The image processing part 23 transmits thus obtained data of a blood vessel image (hereinafter, this is referred to as "blood vessel image data") D23 to the authentication part 24.

The authentication part 24 detects an agreement degree in blood vessel forming pattern between the blood vessel image based on this blood vessel image data D23 and the registered blood vessel image based on the registered blood vessel image data DR read from the flash memory 25. The authentication part 24 determines whether or not the finger FG imaged at that time is of the said registered person by the above agreement degree, and transmits this determination result to the control part 20 as determination data D24.

In this manner, if the control part 20 receives the determination data D24 from the above authentication part 24 by controlling the imaging drive part 22, the image processing part 23 and the authentication part 24 as the above, the control part 20 transfers this determination data D24 to an external device via the external interface IF. At the same time, the control part 20 stops the near infrared light emitting parts 8 and the CCD image pickup device 4 respectively, via the above imaging drive part 22.

In this manner, the control part 20 executes bioauthentication processing in that the presence of the said person (registered person) is determined using blood vessels being a proper formation existing inward of a living body as an object to be authenticated. Thereby, in comparison to the case of using a fingerprint on the surface of a living body or the like as an object, not only direct stealing from a living body but also pretending by a third party to a registered person can be prevented.

(1-4) Operation and Effect by First Embodiment

According to the above configuration, in this authentication apparatus 1, in the top surface 2A of the housing 2, the placing part 7 is provided near the other end of shorter side ED2. The reflective board 6 is provided between the imaging opening part 3 facing to the above placing part 7 and the one end of shorter side ED1. And at a lower part of the above imaging opening part 3 in the housing 2, the CCD image pickup device 4 for transmitting near infrared lights that passed through the finger FG placed on the placing part 7 and was refracted by the reflective board 6 as a blood vessel image signal S1 is provided.

Accordingly, in the authentication apparatus 1, the distance from the CCD image pickup device 4 to the top surface of the imaging opening part 3 and the distance from the top surface of the above imaging opening part 3 to the placing part 7 are connected by the reflective board 6, so that the distance from the above CCD image pickup device 4 to the placing part 7 can be kept longer than a conventional system for the distance from the top surface of the imaging opening part 3 to the placing part 7. Therefore, distortion of aberration in the optical system can be removed, without only relying on correction by a macro lens and a signal processing circuit. Thus, image quality can be improved.

Then, in this authentication apparatus 1, the placing part 7 and the reflective board 6 are disposed so that a light path is formed in almost parallel to the top surface 2A of the housing 2. Therefore, the thickness of the authentication apparatus 1 can be remarkably restrained in comparison to the case of keeping the distance in the thickness direction. Thus, the authentication apparatus 1 can be miniaturized.

Further, in the authentication apparatus 1 as described above, by taking various countermeasures to improve image quality in order to obtain a fine imaging result on the top surface 2A of the housing 2, mixing of the lights in the atmosphere other than imaging lights with the above imaging lights (near infrared lights) emitted to the CCD image pickup device 4 can be reduced. Therefore, image quality can be further improved.

According to the above configuration, in the top surface 2A of the housing 2, the placing part 7 is provided near the other end of shorter side ED2. The reflective board 6 is provided between the imaging opening part 3 facing to the above placing part 7 and the one end of shorter side ED1. And at a lower part of the above imaging opening part 3 in the housing 2, the CCD image pickup device 4 for transmitting near infrared lights that passed through the finger FG placed on the placing part 7 and was refracted by the reflective board 6 as a blood vessel image signal S1 is provided. Thereby, in addition to the distance from the CCD image pickup device 4 to the reflective board 6 in the thickness direction, the distance from the above reflective board 6 to the placing part 7 in the horizontal direction can be kept. Therefore, distortion of aberration in the optical system can be removed without only relying on correction by the macro lens and the signal processing circuit, as well as restraining the entire thickness. Thus, image quality can be improved while considering miniaturization.

(2) Second Embodiment (2-1) Exterior Configuration of Cellular Phone

Figure 6:
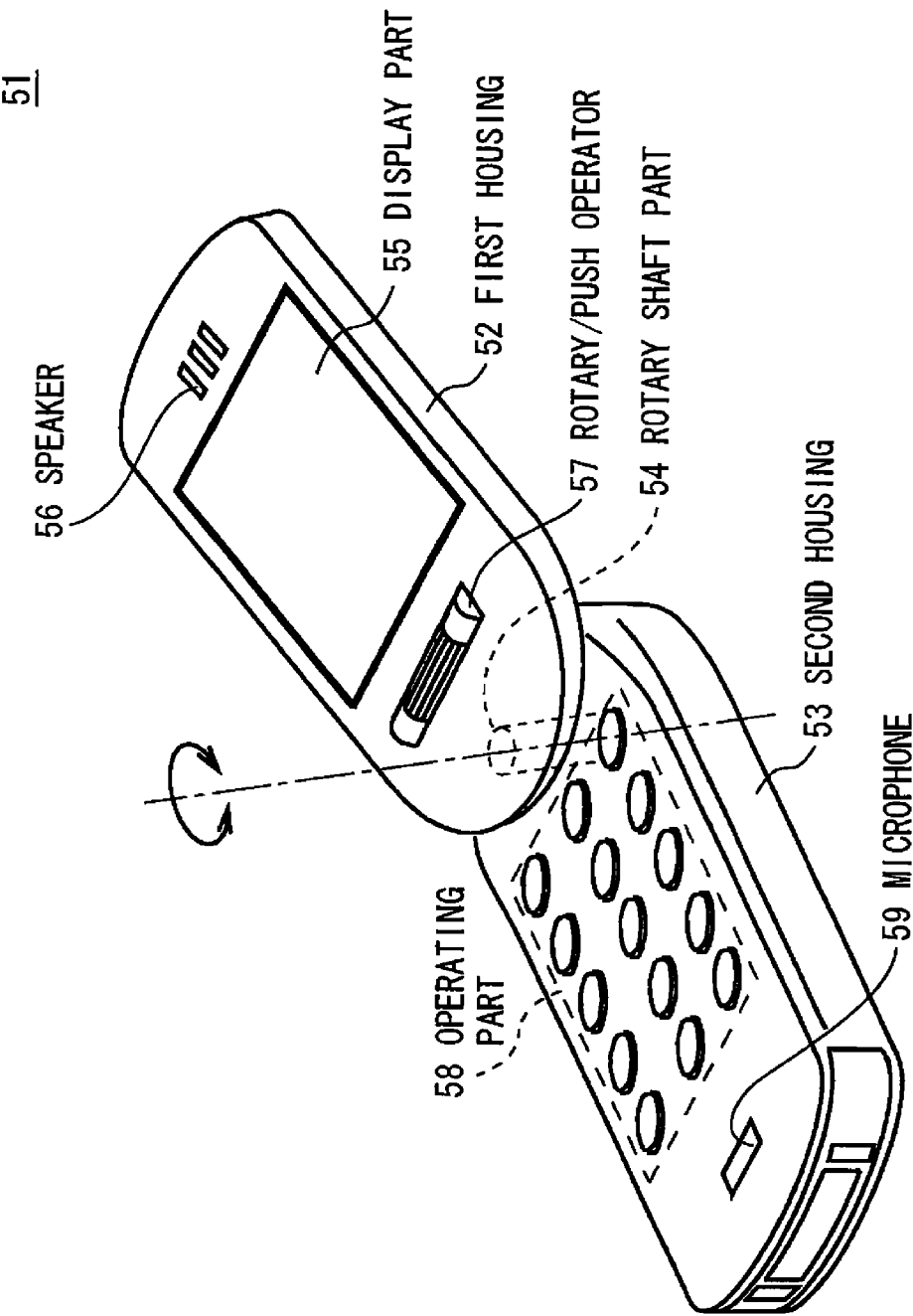
FIG. 6 is a schematic diagram showing the exterior configuration (open state) of a cellular phone.
Figure 7:
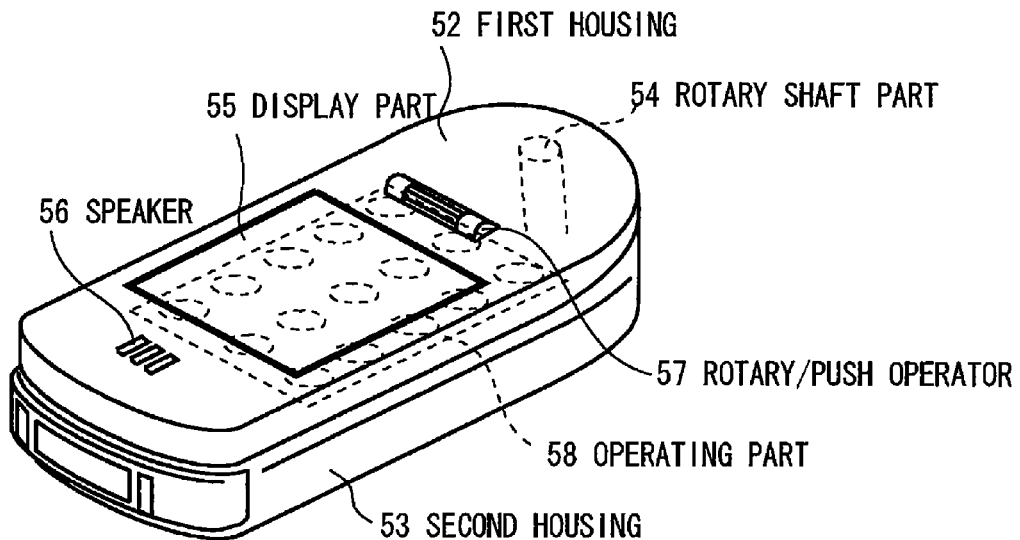
FIG. 7 is a schematic diagram showing the exterior configuration (closed state (1)) of the cellular phone.

Referring to FIGS. 6 and 7, the reference numeral 51 shows a cellular phone according to a second embodiment as a whole. The cellular phone 51 is formed by that a first housing (hereinafter, this is referred to as a "first housing") 52 and a second housing (hereinafter, this is referred to as a "second housing") 53 in an almost rectangular parallelepiped form are connected freely in turn in the almost horizontal direction by a rotary shaft part 54 provided at one end of the above second housing 53.

At the center of the front surface of this first housing 52, a display part 55 is provided. A speaker 56 is provided at a part upper than the above display part 55, and an operator called a jog dial that is freely turned and pressed (hereinafter, this is referred to as a "rotary/push operator") 57 is provided at a part lower than the display part 55, respectively.

On one hand, an operating part 58 composed of various operation keys such as a power key, a call key and a character input key is provided at the center of the front surface of the second housing 53. A microphone 59 is provided at a part lower than the above operating part 58.

In this cellular phone 51, in an open state that the back surface of the first housing 52 and the front surface of the second housing 53 are separated (FIG. 6), call can be performed or the operating part 58 can be operated while holding the second housing 53 with one hand. On the other hand, in a closed state that the back surface of the first housing 52 and the front surface of the second housing 53 are overlapped (FIG. 7), the operating part 58 is protected, and also misoperation is prevented. Further, the overall dimension of the cellular phone 51 can be miniaturized, and the portability can be improved.

Figure 8:
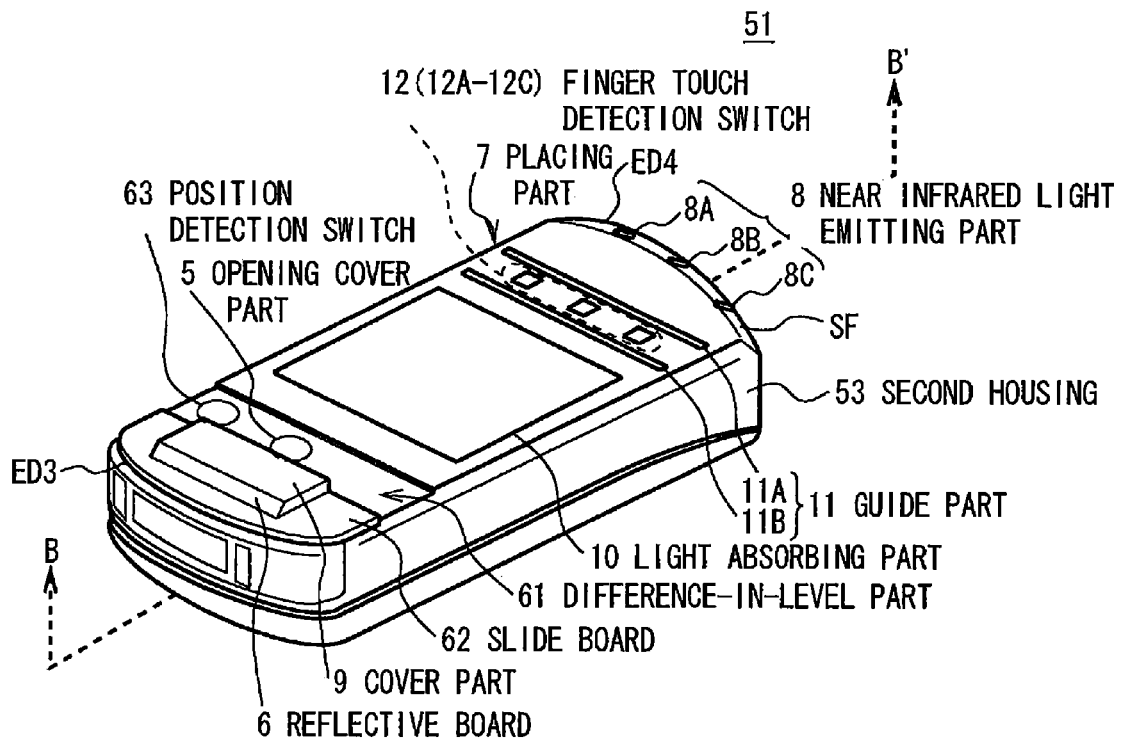
FIG. 8 is a schematic diagram showing the exterior configuration (closed state (2)) of the cellular phone.
Figure 9:
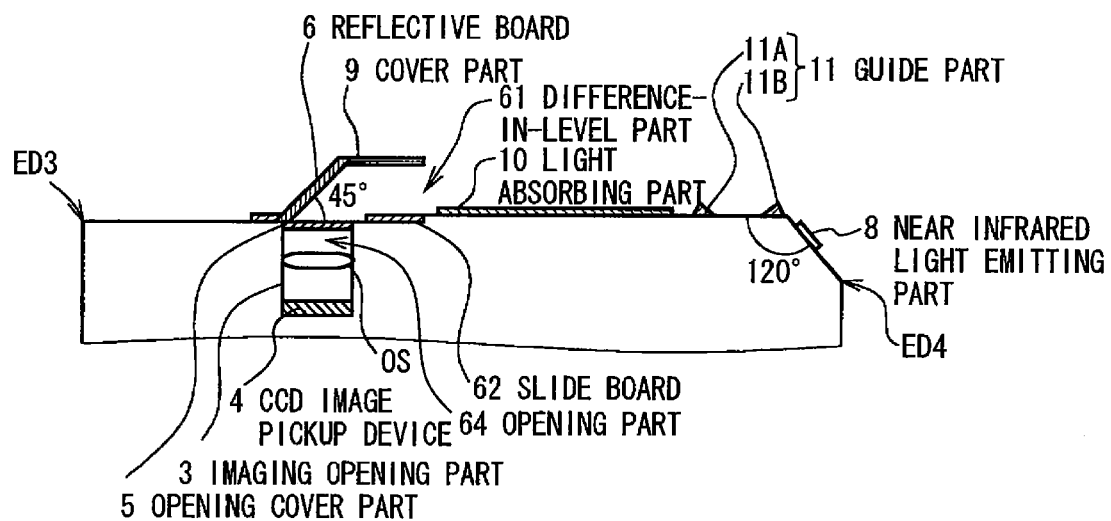
FIG. 9 is a schematic diagram showing the section (1) of a second housing.
Figure 10:
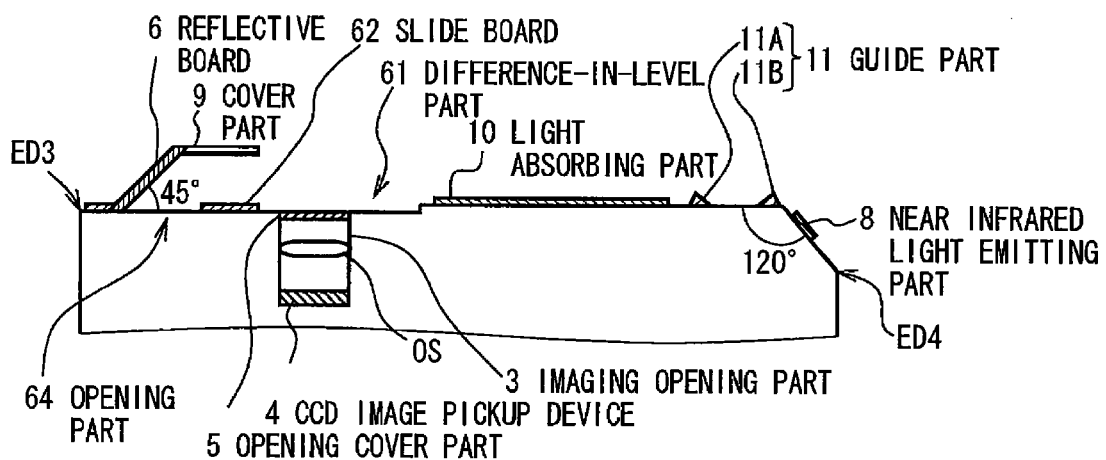
FIG. 10 is a schematic diagram showing the section (2) of the second housing.

On the other hand, on the back surface of this second housing 53, as shown in FIG. 8 in that the same reference numerals are added to corresponding parts to FIG. 1, and FIGS. 9 and 10 by a section by B-B' in FIG. 8, a difference-in-level part 61 in a recessed form is formed near one end of shorter side ED3. At the center of this difference-in-level part 61, an imaging opening part 3 is formed. In the above imaging opening part 3, an opening cover part 5, an optical system part OS and a CCD image pickup device 4 are provided in this order.

Further, in the difference-in-level part 61, a slide board 62 which is freely movable from a position facing to the above CCD camera (CCD image pickup device 4) (hereinafter, this is referred to as a "camera shielding position" (FIG. 9)) to the position of the one end of shorter side ED3 separated from the above camera shielding position (hereinafter, this is referred to as a "camera exposing position" (FIG. 10)) is provided as corresponding to the back surface of the second housing 53.

At a predetermined position on the bottom surface of the difference-in-level part 61, a press-type switch for detecting the camera shielding position or the camera exposing position of the slide board 62 (hereinafter, this is referred to as a "position detection switch") 63 is provided. In this cellular phone 51, in the case where the camera exposing position (FIG. 10) was recognized based on the detection result by the above position detection switch 63, an object such as a background and a person can be imaged.

In addition to the above configuration, in the slide board 62, a reflective board 6 and a cover part 9 are held so as to fit on an opening part 64 provided as digged at its center. Thereby, the above reflective board 6 and cover part 9 can be freely moved from the camera shielding position (FIG. 9) to the camera exposing position (FIG. 10).

Further, on the other end of shorter side ED4, a slant surface SF is formed so as to form an inclination angle of 120 degrees to the back surface of the second housing 53. On the above slant surface SF, near infrared light emitting parts 8 (8A, 8B and 8C) for emitting near infrared lights to a placing part 7 in an wavelength band that is uniquely absorbed by both of oxygenated hemoglobin and deoxygenated hemoglobin (approximately 900 [nm]-1000 [nm]) are provided.

The placing part 7 to place a finger is provided near this other end of shorter side ED4. In the above placing part 7, a pair of guide parts 11 (11A and 11B) to guide a finger FG are provided so that the belly of the finger FG is orthogonal to the top surface 2A. Between the above guide parts 11, three finger touch detection switches 12 (12A, 12B and 12C) are provided along the guide direction, at predetermined intervals.

Figure 11:
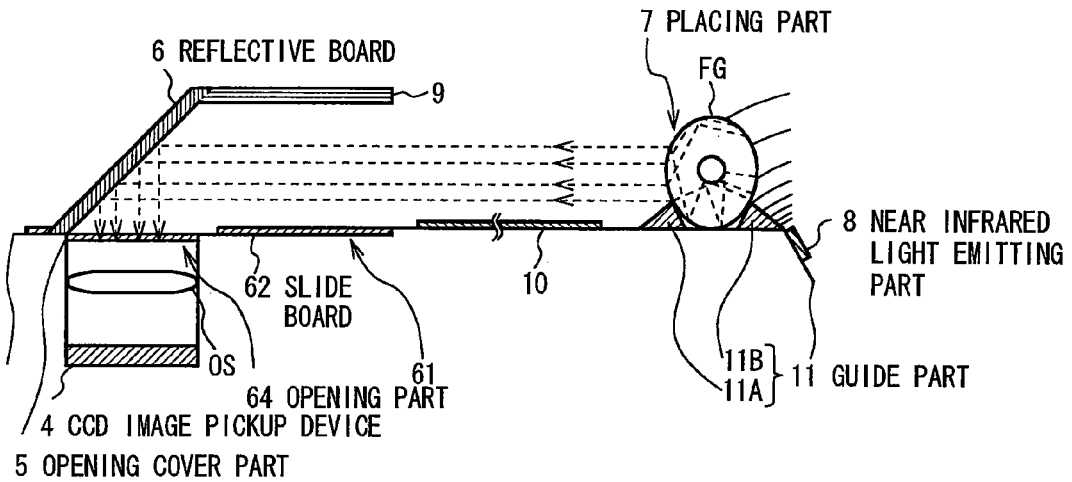
FIG. 11 is a schematic diagram for explaining the light path of near infrared lights in the second housing.

Therefore, in this cellular phone 51, as shown in FIG. 11, if the slide board 62 is at the camera shielding position (FIG. 9) and a finger FG is placed between the pair of guide parts 11A and 11B in the placing part 7, near infrared lights emitted from the near infrared light emitting parts 8 are emitted to the above finger FG, pass through the inside of the finger FG, and are emitted from the above finger FG as blood vessel projecting lights. Then, the blood vessel projecting lights which are almost parallel to the back surface of the second housing 53 are emitted to a space formed by the slide board 62 and the cover part 9, are refracted by the reflecting surface RF of the above reflective board 6, and are incident to the CCD image pickup device 4 sequentially via the opening part 64, the opening cover part 5 and the optical system part OS. As a result, blood vessels in the finger FG are imaged by the CCD image pickup device 4, and the imaging result is transmitted as a blood vessel image signal.

In the case of this embodiment, in the cellular phone 51, in the case where the camera shielding position of the slide board 62 (FIG. 9) was recognized based on the detection result by the position detection switch 63 and being the finger FG parallel was recognized based on the detection result by the finger touch detection switches 12A, 12B and 12C, blood vessels in the above finger FG can be automatically imaged.

Consequently, when in not performing imaging of an object, a user of this cellular phone 51 usually sets the slide board 62 to the camera shielding position (FIG. 9). Thus, when in imaging blood vessels, the user can image the blood vessels only a necessary action that the user places his/her finger FG between the guide parts 11.

Further, in the cellular phone 51 in this embodiment, at the time of imaging an object, near infrared lights emitted from the near infrared light emitting parts 8 can be also used as a flash. Thus, the cellular phone 51 can be miniaturized for that a light source dedicated to flash is omitted.

(2-2) Circuit Configuration of Cellular Phone

Figure 12:
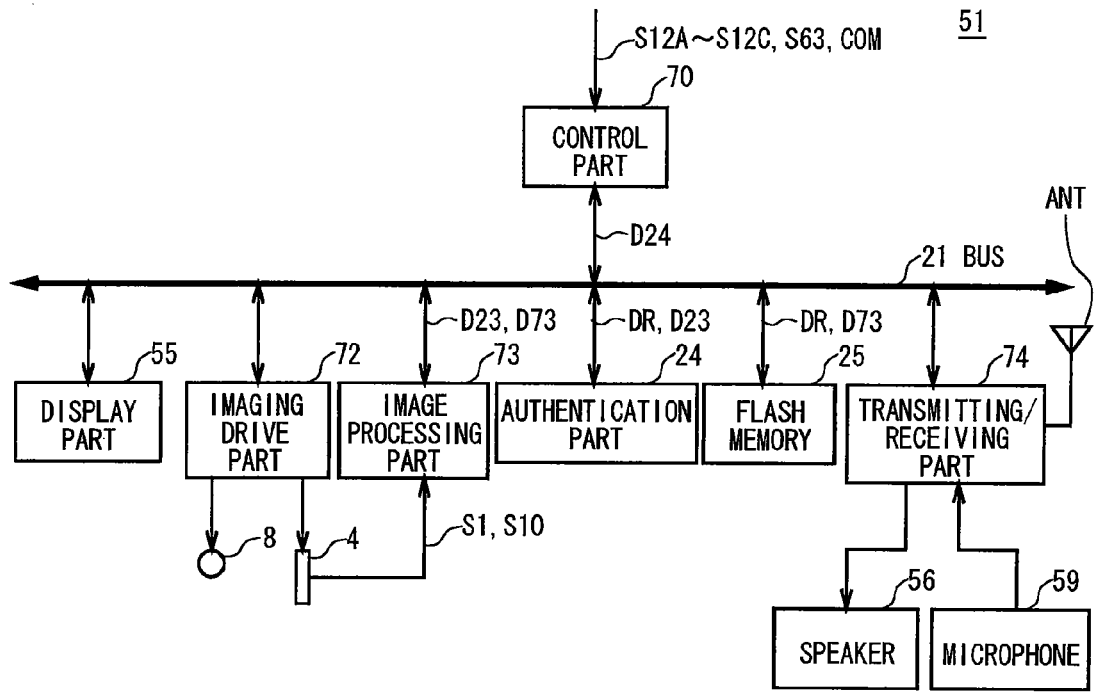
FIG. 12 is a block diagram showing the circuit configuration of the cellular phone.

The circuit configuration of this cellular phone 51 is shown in FIG. 12 in that the same reference numerals are added to corresponding parts in FIG. 5.

Referring to FIG. 12, the cellular phone 51 is formed by that a display part 55, an imaging drive part 72, an image processing part 73, an authentication part 24, a flash memory 25 and a transmitting/receiving part 74 are connected to a control part 70 respectively via a bus 21. In the flash memory 25, for example, when this cellular phone 51 was purchased, blood vessels in the finger FG of the user who purchased it is registered by a predetermined blood vessel registration system, as the data of a registered blood vessel image (registered blood vessel image data) DR.

The control part 70 has a computer configuration including a CPU (Central Processing Unit) for controlling the entire authentication apparatus 1, a ROM (Read Only Memory) to store various programs, and a RAM (Random Access Memory) serving as a work memory of the above CPU. To the above control part 70, corresponding detection signals S12A to S12C are supplied from three finger touch detection switches 12A to 12C (FIG. 8) respectively, and a position detection signal S63 is supplied from a position detecting switch 63 (FIG. 8).

Further, to this control part 70, commands that correspond to various buttons in an operating part 58 respectively, and commands that correspond to a rotating operation and a pressing operation of a rotary/push operator 57 respectively are supplied from the operating part 58 and the rotary/push operator 57 as execution commands COM.

The control part 70 recognizes that the finger FG is parallel based on the above detection signals S12A-S12C, and also recognizes a camera shielding position (FIG. 9) or a camera exposing position (FIG. 10) based on the above position detection signal S63. Based on these recognition results, execution command COM and programs stored in the ROM, the control part 70 properly controls the display part 55, the imaging drive part 72, the image processing part 73, the authentication part 24, the flash memory 25 and the transmitting/receiving part 74.

When in imaging blood vessels inward of a finger, the imaging drive part 72 drives a near infrared light emitting part 8 and a CCD image pickup device 4 respectively. In this case, to a finger FG that is placed between a pair of guide parts 11A and 11B (FIG. 8) at this time, near infrared lights are emitted from the near infrared light emitting part 8. Blood vessel projecting lights induced in a CCD camera (CCD image pickup device 4) through the above finger FG are transmitted from this CCD camera (CCD image pickup device 4) to the image processing part 73, as a blood vessel image signal S1.

On the other hand, when in imaging an object, the imaging drive part 72 drives the CCD camera (CCD image pickup device 4), and also drives the near infrared light emitting part 8 as the occasion demands, so that near infrared lights are emitted as a flash. Then, the imaging drive part 72 controls the diaphragm of an optical system part OS by automatic exposure control processing, and adjusts an amount of light of lights that are incident to the CCD image pickup device 4. At the same time, the imaging drive part 72 controls the position of a lens in the optical system part OS by autofocus control processing, and adjusts a focal distance and a focus position. In this case, the image of an object formed on this CCD image pickup device 4 is transmitted from the above CCD image pickup device 4 to the image processing part 73 as an image signal (hereinafter, this is referred to as an "object image signal") S10.

In the case where the blood vessel image signal S1 was supplied from the CCD image pickup device 4, the image processing part 73 sequentially performs analog-to-digital conversion processing, various filtering processing for noise component elimination and outline emphasis or the like, binarization processing, and blood vessel linearization processing called Morphology on the above blood vessel image signal S1, for example, similarly to the case of the aforementioned first embodiment, and generates blood vessel image data D23.

On the other hand, in the case where the object image signal S10 was supplied from the CCD image pickup device 4, the image processing part 73 performs compressive coding processing based on a compressive coding method called JPEG (Joint Photographic Experts Group), for example, on the above object image signal S10, and generates compressed image data D73.

The transmitting/receiving part 74 is connected to the speaker 56, the microphone 59 and an antenna ANT provided in this cellular phone 51, respectively. The transmitting/receiving part 74 modulates a signal supplied from the above microphone 59 or the control part 70 and then amplifies the signal, and transmits thus obtained uplink signal to a base station (not shown) via the antenna ANT.

On the other hand, the transmitting/receiving part 74 receives a downlink signal transmitted from the base station (not shown) via the antenna ANT, amplifies this and then demodulates the signal, and transmits thus obtained signal to the speaker 56 or the control part 70.

(2-3) Concrete Processing Contents by Control Part

Next, concrete processing contents by the above control part 70 will be described.

This cellular phone 51 has an illegal access preventing function to forbid an access to the flash memory 25 until the user is judged as a registered person.

Practically, the control part 70 shifts the operation mode to an illegal access forbidding mode responding to power on. In the illegal access forbidding mode, in each processing respectively corresponding to various functions that the cellular phone 51 has, execution of target processing previously set is restrained.

In the case of this embodiment, access processing to the flash memory 25 has been set as target processing. The control part 70 does not accept an execution command COM concerning access to the flash memory 25 such as object imaging processing and e-mail transmitting processing.

That is, in this illegal access forbidding mode, if a position detection signal S63 showing the camera exposing position of the slide board 62 (FIG. 10) is supplied from the position detection switch 63 (FIG. 8), the control part 70 displays a content such as "Image pickup is unavailable until you are confirmed as the said registered person. Please make authentication." for example, on the display part 55, without executing object imaging processing, and notifies the user of that bioauthentication processing should be executed before executing object imaging processing.

Further, also in the case where an execution command COM showing e-mail transmitting processing or the like was received, the control part 70 notifies the user of that bioauthentication processing should be executed before executing object imaging processing without executing the above e-mail transmitting processing or the like.

On one hand, in this illegal access forbidding mode, in the state where the position detection signal S63 showing the camera shielding position of the slide board 62 (FIG. 9) has been supplied from the position detection switch 63 (FIG. 8), if all of the detection signals S12A, S12B and S12C are supplied from the corresponding finger touch detection switches 12A, 12B and 12C (FIG. 1), the control part 70 executes bioauthentication processing.

In this case, the control part 70 controls the imaging drive part 72 so as to drive the CCD image pickup device 4 and the near infrared light emitting parts 8, and controls the image processing part 73 so as to perform various processing such as blood vessel linearization processing on a blood vessel image signal S1 transmitted from the above CCD image pickup device 4.

Then, the control part 70 transmits blood vessel image data D23 generated in the above image processing part 73 and registered blood vessel image data DR previously registered in the flash memory 25 to the authentication part 24, and controls the authentication part 24 so as to determine the presence of the said registered person based on these blood vessel image data D23 and registered blood vessel image data DR.

Here, if determination data D24 supplied from the authentication part 24 as the above determination result is data that shows being not the said registered person, the control part 70 controls the imaging drive part 72 so as to drive the CCD image pickup device 4 and the near infrared light emitting part 8, and keeps this illegal access forbidding mode.

On the contrary, if the determination data D24 is data that shows being the said registered person, the control part 70 controls the imaging drive part 72 so as to drive the CCD image pickup device 4 and the near infrared light emitting part 8, and shifts the operation mode from this illegal access forbidding mode to a usual use mode.

In this manner, the control part 70 can execute bioauthentication processing.

On the other hand, in the above use mode, if a position detection signal S63 showing the camera exposing position of the slide board 62 (FIG. 10) is supplied from the position detection switch 63 (FIG. 8), the control part 70 executes object imaging processing.

In this case, the control part 70 controls the imaging drive part 72 so as to drive the CCD image pickup device 4, and also controls the imaging drive part 72 so as to adjust the lens position of the optical system part OS and an amount of light to the CCD image pickup device 4. At this time, if an execution command COM showing a flash lighting instruction is supplied, the control part 70 controls the imaging drive part 72 so as to emit near infrared lights from the near infrared light emitting part 8 as a flash.

Then, if an execution command COM showing an imaging instruction is supplied in the above state, the control part 70 controls the image processing part 73 so as to perform image compression processing on an object image signal S10 transmitted from the CCD image pickup device 4 at this time, and stores thus obtained compressed image data D73 in the flash memory 25.

In this manner, the control part 70 can execute object imaging processing.

Note that, in this use mode, also in the case where an execution command COM showing e-mail transmitting processing or the like was received, the control part 70 executes corresponding various processing without restriction.

In this manner, in this cellular phone 51, access to the flash memory 25 is forbidden until the user is determined as a registered person, so that the contents of various data stored in the flash memory 25 can be protected from a third party.

(2-4) Operation and Effect By Second Embodiment

According to the above configuration, in this cellular phone 51, the placing part 7 is provided near the other end of shorter side ED4 on the back surface of the second housing 53, and the reflective board 6 is provided between the imaging opening part 3 facing to the above placing part 7 and the one end of shorter side ED3. And the CCD image pickup device 4 for transmitting near infrared lights that passed through the finger FG placed on the placing part 7 and were refracted by the reflective board 6 as a blood vessel image signal S1 is provided at a lower part of the above imaging opening part 3 in the second housing 53.

Accordingly, in this cellular phone 51, similarly to the case of the aforementioned first embodiment, in addition to the distance from the CCD image pickup device 4 to the reflective board 6 in the thickness direction, the distance from the above reflective board 6 to the placing part 7 in the horizontal direction can be kept. Therefore, distortion of aberration in the optical system can be removed without only relying on correction by a macro lens and a signal processing circuit, as well as restraining the overall thickness. Thus, image quality can be improved while considering miniaturization.

In addition to this, in this cellular phone 51, the above reflective board 6 can be held freely movably from the camera shielding position facing to the CCD image pickup device 4 (FIG. 9) to the camera exposing position separated from the above camera holding position (FIG. 10), and according to the above holding position, processing on a signal transmitted from the CCD image pickup device 4 is switched to bioauthentication processing or image compression processing.

Accordingly, in this cellular phone 51, the optical system part OS and the CCD image pickup device 4 can be shared. Thus, the cellular phone 51 can be miniaturized as a whole.

According to the above configuration, the reflective board 6 is held freely movably from the camera shielding position facing to the CCD image pickup device 4 (FIG. 9) to the camera exposing position separated from the above camera shielding position (FIG. 10), and according to the above holding position, processing on a signal transmitted from the CCD image pickup device 4 is switched to bioauthentication processing or image compression processing. Thereby, the above CCD image pickup device 4 can be shared. Thus, the cellular phone 51 can be miniaturized as a whole.

(3) Other Embodiments

In the aforementioned embodiment, it has dealt with the case where in the first embodiment, a bioimaging apparatus for imaging a formation in a bioregion as an object to be imaged is applied to a dedicated authentication apparatus 1 having an authentication function, and in the second embodiment, the bioimaging apparatus is applied to a cellular phone 51 having an authentication function. However, the present invention is not only limited to this but also an imaging apparatus in this invention can be applied to apparatuses having various uses other than this, such as application to medical equipment.

Further, in the aforementioned embodiment, as a formation, it has dealt with the case where blood vessels are applied. However, the present invention is not only limited to this but also various formations other than this such as nerves existing inward of a living body, a fingerprint and a mouthprint existing on the surface of a living body can be applied. In this connection, in the case of applying nerves, for example, if a marker unique to nerves is injected in a body and the marker is imaged, the nerves can be imaged similarly to the aforementioned embodiment.

Further, in the aforementioned embodiment, as a bioregion, it has dealt with the case where a finger is applied. However, the present invention is not only limited to this but also various bioregions other than this such as a palm, an arm and an eye can be applied, depending on an object to be imaged.

Further, as the configuration of an imaging apparatus, it has dealt with the case where in the first embodiment, the authentication apparatus 1 having the configuration shown in FIGS. 1 and 2 is applied, and in the second embodiment, the cellular phone 51 having the configuration shown in FIGS. 6-10 is applied. However, the present invention is not only limited to this but also depending on a use, an object to be imaged, or the like, the arrangement, the shape or the configuration of each part concerning the above imaging may be properly changed.

That is, in the aforementioned embodiment, as a placing part that is provided on the front surface side of a housing containing an electronic circuit to place a bioregion, it has dealt with the case where it is provided on the top surface 2A of the housing 2 (the back surface of the second housing 53). However, instead of this, for example, a difference-in-level part is provided in the direction orthogonal to the top surface 2A (the back surface of the second housing 53), and a part of or all of the difference-in-level part may be used as a placing part.

Further, in the aforementioned embodiment, it has dealt with the case where the placing part 7 formed by the pair of guide parts 11A and 11B and the finger touch detection switches 12A-12C are applied. However, the present invention is not only limited to this but also the number of the above finger touch detection switches 12 may be changed, or the shape or the configuration of the guide part 11 may be modified. Either one of them may be omitted. Or instead of omitting both of them, a mark for a placement may be provided on the surface. Further, a placing part formed by combining the aforementioned contents may be adopted.

Next, in the aforementioned embodiment, as an emitting part for emitting imaging lights to a placing part, near infrared lights of 900 [nm]-1000 [nm] are emitted. However, instead of this, lights on various wavelengths other than this such as visible lights may be emitted.

Further, in the aforementioned embodiment, as a method for attaching an emitting part, it has dealt with the case where it is provided on the top surface 2A of the housing 2 (the back surface of the second housing 53). However, instead of this, an emitting part may be provided as buried in the above top surface 2A (the back surface). A member to dispose an emitting part is provided in a space on the above top surface 2A (the back surface of the second housing 53), and the emitting part may be provided on that member. However, in the case of considering the thickness of an overall apparatus, it is desirable to be provided on the top surface 2A of the housing 2 (the back surface of the second housing 53) or in a space near that.

Further, in the aforementioned embodiment, as an emitting direction of imaging lights, imaging lights are emitted from the direction forming 120 degrees to the top surface 2A of the housing 2 (the back surface of the second housing 53), however, imaging lights can be emitted from any directions. However, in the case of emitting imaging lights to a formation existing inward of a living body as blood vessels applied in the aforementioned embodiment, if considering the thickness of an overall apparatus, it is desirable that an emitting part is provided so as to be an emitting direction forming an obtuse angle to the placing surface of a placing part. Specifically, it is preferable to select any one of angles from 100 degrees to 140 degrees to the placing surface of a placing part.

Next, in the aforementioned embodiment, as a reflective board that is provided as facing to a placing part on the front surface side of a housing, and reflects imaging lights from a bioregion placed on the placing part to the inside of a housing, it has dealt with the case where the reflective board is provided in the state slant to the other end of shorter side ED2 (the other end of shorter side ED4) so as to form an inclination angle of 45 degrees to the top surface 2A of the housing 2 (the back surface of the second housing 53). However, instead of this, for example, a difference-in-level part is provided in the direction orthogonal to the top surface 2A (the back surface of the second housing 53), and a reflective board may be provided on the difference-in-level part. A member to dispose a reflective board in a space on the above top surface 2A (the back surface of the second housing 53) is provided, and the reflective board may be provided on the member. Further, as an inclination angle, also an angle other than 45 degrees can be selected.

Next, in the aforementioned embodiment, as an image pickup device that is provided in a housing, and transmits imaging lights reflected by a reflective board as an image signal, it has dealt with the case where the CCD image pickup device 4 is applied. However, instead of this, various image pickup devices other than this such as a CMOS (Complementary Metal Oxide Semiconductor) can be applied. Further, also as to a position disposing this, an image pickup device can be disposed at various positions in a housing.

Next, in the aforementioned embodiment, as inclination detection means for detecting inclination of a finger or a hand guided by a guide part, it has dealt with the case where the finger touch detection switches are provided along the guide direction at predetermined intervals. However, instead of the above finger touch detection switches, a camera may be provided, or detection mechanism for mechanically detecting inclination may be provided.

In this case, in the aforementioned embodiment, it has dealt with the case where the presence of inclination is detected. However, an inclination angle may be detected, and this may be notified.

Further, in the aforementioned embodiment, it has dealt with the case where the reflective board 6 is covered except the incident path and the reflecting path of imaging lights to the reflecting surface of the reflective board 6. However, the present invention is not only limited to this but also all over the top surface 2A of the housing 2 (the back surface of the second housing 53) may be covered.

Figure 13:
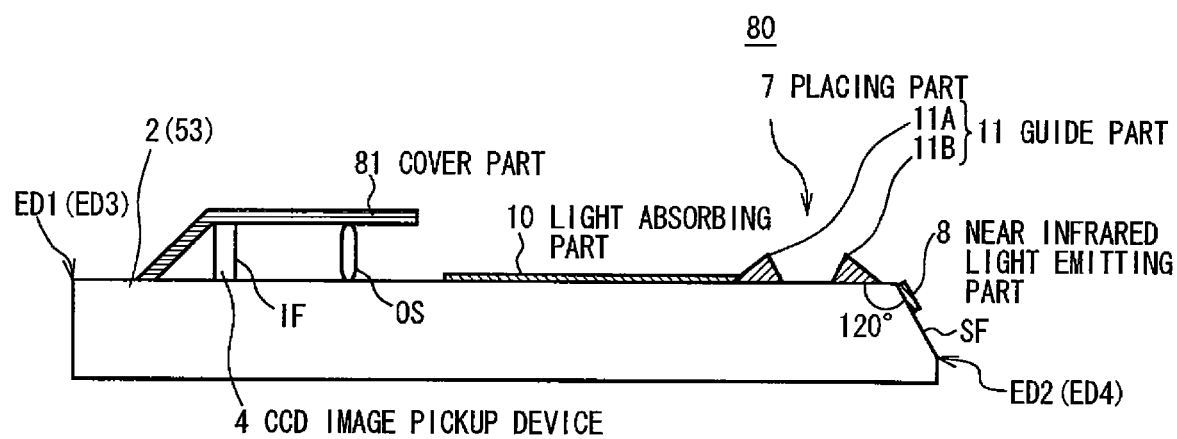
FIG. 13 is a schematic diagram showing the configuration of an imaging apparatus in other embodiment.

Further, in the aforementioned embodiment, as an imaging apparatus, it has dealt with the case where in the first embodiment, the apparatus having the configuration shown in FIGS. 1 and 2 is applied, and in the second embodiment, the apparatus having the configuration shown in FIGS. 6-10 is applied. However, the present invention is not only limited to this but also an imaging apparatus 80 having a configuration shown in FIG. 13 in that the same reference numerals are added to corresponding parts in FIG. 2 and FIG. 9 may be applied.

This imaging apparatus 80 is largely different from the authentication apparatus 1 (the cellular phone 51) contained in the housing 2 (the second housing 53) in a point that the imaging system formed by the optical system part OS and the CCD image pickup device 4 is disposed on the top surface 2A of the housing 2 (the back surface of the second housing 53). Further, in the imaging apparatus 80, it is different from the cover part 9 that covers the reflective board 6 except the incident path and the reflecting path of imaging lights to the reflecting surface of the reflective board 6, in a point that a cover part 81 covering the above optical system part OS and CCD image pickup device 4 except the incident direction to the imaging surface IF is provided.

According to this imaging apparatus 80, the optical system part OS and the CCD image pickup device 4 are provided on the front surface of the housing 2 (the second housing 53) as facing to the placing part 7. Thereby, a distance in the horizontal direction can be kept on the front surface of the above housing 2 (the second housing 53), without containing an imaging system in the housing 2 (the second housing 53) that contains an electronic circuit. Therefore, distortion of aberration in the optical system can be removed without only relying on correction by a macro lens and a signal processing circuit, as well as reducing the thickness of the above housing 2 (the second housing 53) itself and restraining the overall thickness.

Note that, as the slide board 61 in the second embodiment, by mounting a holding part that holds the optical system part OS, the CCD image pickup device 4 and the cover part 81 freely movable from a first position to a second position that is separated from the first position, the distance between the CCD image pickup device 4 and the placing part 7 may be adjusted according to the diameter of a finger placed on the placing part 7. Thereby, image quality can be further improved.

INDUSTRIAL APPLICABILITY

The present invention can be utilized in a field that uses a technique for identifying a living body and a medical field.

The invention claimed is:

1. A bioimaging apparatus for imaging a formation in a bioregion as an object to be imaged, comprising:
    a placing part, to place said bioregion, positioned on the front surface side of a housing containing an electronic circuit;
    an emitting part for emitting imaging lights to said placing part;
    a reflective board, for reflecting said imaging lights which are transmitted through said bioregion placed on said placing part to the inside of said housing, positioned on the front surface side of said housing facing said placing part; and
    an image pickup device for transmitting said imaging lights reflected by said reflective board as an image signal, provided in said housing;
    wherein said bioregion is a finger or a hand; and
    said placing part is formed by a guide part to guide said finger or said hand so that the belly of the finger or the palm is almost orthogonal to a placing surface.

2. The bioimaging apparatus according to claim 1, wherein:
    said object to be imaged is a formation existing in said bioregion; and
    said emitting part is provided as being in an emitting direction having an obtuse angle to a placing surface of said placing part.

3. The bioimaging apparatus according to claim 1, wherein:
    said object to be imaged is a formation existing in said bioregion; and
    said emitting part is provided as being in an emitting direction having any one of angles from 100 degrees to 140 degrees to the placing surface of said placing part.

4. The bioimaging apparatus according to claim 1, wherein:
    said object to be imaged is a formation existing in said bioregion; and
    said emitting part emits said imaging lights having an wavelength unique to said object to be imaged.

5. The bioimaging apparatus according to claim 4, wherein said emitting part emits said imaging lights comprising a wavelength uniquely absorbed by oxygenated hemoglobin and deoxygenated hemoglobin.

6. The bioimaging apparatus according to claim 5, wherein said emitting part emits said imaging lights comprising a wavelength of about 900 nm to about 1,000 nm.

7. The bioimaging apparatus according to claim 1, including:

a sheet-form light absorbing part for absorbing said imaging lights, provided between said placing part and said reflective board.

8. The bioimaging apparatus according to claim 1, including;

a cover part for covering a reflecting surface except the incidental path and the reflecting path of said imaging lights to the reflecting surface of said reflective board.

9. The bioimaging apparatus according to claim 1, wherein:

said placing part is further formed by inclination detection means for detecting the inclination of said finger or said hand guided by said guide part; and drive means for driving said emitting part and said image pickup device according to the detection result by said inclination detection means is included.

10. The bioimaging apparatus according to claim 1, wherein:

said placing part is further formed by inclination detection means for detecting the inclination of said finger or said hand guided by said guide part; and notification means for notifying the state of said inclination according to the detection result by said inclination detection means is included.

11. The bioimaging apparatus according to claim 1, comprising:

a holding part for holding said reflective board freely movably from a first position facing to said image pickup device to a second position separated from the above first position;

position detection means for detecting said holding part;

image processing means for performing image processing on an image signal transmitted from said image pickup device; and control means for controlling said image processing means so as to perform image processing suitable to an object to be imaged existing inward of said bioregion, or image processing according to an object other than the above object to be imaged, suitable to the position of said holding part detected by said position detection means.

12. The bioimaging apparatus according to claim 1, comprising:

a holding part for holding said reflective board freely movably from a first position facing to said image pickup device to a second position separated from the above first position;

position detection means for detecting the position of said holding part;

touch detection means for detecting a touch of said bioregion to said placing part; and drive means for driving said emitting part and said image pickup device, when said first position and a touch of said bioregion were detected.

* * * * *